United States Patent [19]

Naisby et al.

[11] Patent Number: 5,273,997
[45] Date of Patent: Dec. 28, 1993

[54] BIOCIDAL COMPOUNDS

[75] Inventors: Thomas W. Naisby; William W. Wood, both of Sittingbourne, England; Werner E. J. Simon, Jugenheim, Fed. Rep. of Germany

[73] Assignee: Shell Research Limited, United Kingdom

[21] Appl. No.: 897,667

[22] Filed: Jun. 12, 1992

[30] Foreign Application Priority Data

Jun. 13, 1991 [GB] United Kingdom ............... 9112697

[51] Int. Cl.⁵ ............... A61K 31/335; A61K 31/36; C07D 317/66
[52] U.S. Cl. ............................ 514/452; 549/336; 549/362; 549/439; 514/466
[58] Field of Search ............ 549/336, 362, 439; 514/452, 466

[56] References Cited

U.S. PATENT DOCUMENTS 4,427,666  1/1984  Mues et al. ..................... 514/452
4,971,981 11/1990  Karrer ........................... 549/362

FOREIGN PATENT DOCUMENTS 371560  6/1990  European Pat. Off. .

Primary Examiner—Marianne M. Cintins
Assistant Examiner—John Peabody

[57] ABSTRACT

The invention provides compounds of general formula

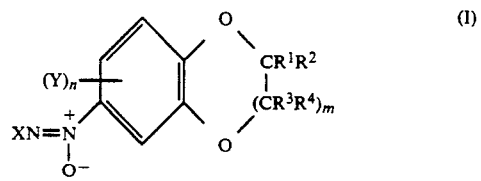

wherein m is 0 or 1; each of $R^1$ and $R^2$, and $R^3$ and $R^4$ if present, independently represents a hydrogen or halogen atom or an optionally substituted alkyl, cycloalkyl or aryl group, or $R^1$ and $R^2$ together or $R^3$ and $R^4$ together represent an optionally substituted alkylene chain; X represents a cyano group, a group —COOH or a salt, ester or amido derivative thereof; Y represents an alkyl group or a halogen atom; and n represents 0, 1, 2 or 3; a process for their preparation; compositions containing such compounds and their use as fungicides.

10 Claims, No Drawings

BIOCIDAL COMPOUNDS

The present invention relates to certain arylazoxycyanides, a process for their preparation, compositions containing such compounds and their use as biocides, especially fungicides.

EP 371560 (Shell) discloses a method of combating a fungus, and/or bacterium, and/or yeast, and/or nematode, at a locus, which comprises treating the locus with a compound of general formula

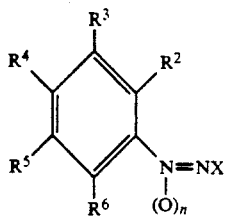

wherein $R^2$ and $R^3$ together, or $R^3$ and $R^4$ together, represent an optionally substituted hydrocarbyloxy chain; the ring is optionally substituted at any or each of the remaining sites $R^5$, $R^6$ and $R^2$ or $R^4$; n represents 0 or 1; and X represents a cyano group, a group —COOH or a salt, ester or amido derivative thereof.

The term "hydrocarbyloxy chain" is used to denote a carbon atom chain interrupted within the chain by one or more (but preferably one only) oxygen atom. In each of the examples, the hydrocarbyloxy chain is interrupted within the chain by one oxygen atom.

The present invention is based on the discovery of certain novel compounds, and the subsequent discovery of their effectiveness in combating fungi.

According to a first aspect of the invention, there are provided compounds of general formula

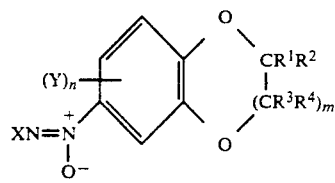

wherein m is 0 or 1; each of $R^1$ and $R^2$, and $R^3$ and $R^4$ if present, independently represents a hydrogen or halogen atom or an optionally substituted alkyl, cycloalkyl or aryl group, or $R^1$ and $R^2$ together or $R^3$ and $R^4$ together represent an optionally substituted alkylene chain; X represents a cyano group, a group —COOH or a salt, ester or amido derivative thereof; Y represents an alkyl group or a halogen atom; and n represents 0, 1, 2 or 3.

When the compounds of the present invention contain an alkyl substituent group, this may be linear or branched and may contain up to 12, preferably up to 6, and especially up to 4, carbon atoms. A cycloalkyl group may contain 3 to 8, preferably 3 to 6, carbon atoms. An aryl group may be any aromatic hydrocarbon group, especially a phenyl or naphthyl group.

Unless otherwise stated in this specification, when any of the foregoing substituent groups are designated as being optionally substituted, the substituent groups which are optionally present may be any one or more of those customarily employed in the development of biocidal compounds and/or the modification of such compounds to influence their structure/activity, persistence, penetration or other property. Specific examples of such substituents include, for example, halogen, especially fluorine, chlorine or bromine atoms, nitro, cyano, hydroxyl, alkyl, haloalkyl (especially $CF_3$), alkoxy, haloalkoxy, amino, alkylamino, dialkylamino, formyl, alkoxycarbonyl, phenoxycarbonyl, benzyloxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms. Typically, 0–3 substituents may be present, most commonly 0 or 1.

Preferably, each of $R^1$ and $R^2$ independently represents a hydrogen atom or a $C_{1-6}$ alkyl, $C_{3-6}$ cycloalkyl, phenyl or naphthyl group or $R^1$ and $R^2$ together represent a $C_{4-6}$ alkylene chain, each group or chain being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl and benzyloxycarbonyl groups.

More preferably, each of $R^1$ and $R^2$ independently represents a hydrogen atom or a $C_{1-6}$ alkyl, $C_{3-6}$ cycloalkyl, phenyl or naphthyl group, each group being optionally substituted by one or more substituents selected from halogen atoms, $C_{1-4}$ haloalkyl, $C_{1-4}$ alkoxycarbonyl and benzyloxycarbonyl groups, or $R^1$ and $R^2$ together represent an unsubstituted $C_{4-6}$ alkylene chain.

It is especially preferred that one of $R^1$ and $R^2$ represents a hydrogen atom or a $C_{1-4}$ alkyl, especially methyl, group and the other of $R^1$ and $R^2$ represents a hydrogen atom or a $C_{1-6}$ alkyl group optionally substituted by a $C_{1-4}$ alkoxycarbonyl or benzyloxycarbonyl group, a $C_{3-6}$ cycloalkyl group, a phenyl group optionally substituted by a halogen atom or $C_{1-4}$ haloalkyl group or a naphthyl group, or $R^1$ and $R^2$ together represent an unsubstituted $C_{4-6}$ alkylene chain.

Where each of R1 and R2 independently represents a halogen atom, the halogen atom is preferably a fluorine or chlorine atom.

It is preferred that each of $R^3$ and $R^4$, if present, independently represents a hydrogen atom or a $C_{1-6}$ alkyl, $C_{3-6}$ cycloalkyl, phenyl or naphthyl group or $R^3$ and $R^4$ together represent a $C_{4-6}$ alkylene chain, each group or chain being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl and benzyloxycarbonyl groups. Most preferably, each of $R^3$ and $R^4$ represents a hydrogen atom.

It is preferred that m is 0.

Preferably, X represents a cyano group, a group —COOH or a group —COOZ where Z represents a $C_{1-4}$ alkyl, $C_{2-4}$ alkenyl or $C_{2-4}$ alkynyl group, for example methyl, ethyl, allyl or propargyl. Most preferably, X represents a cyano group.

Preferably, Y represents a fluorine or chlorine atom or a methyl group. Preferably, n represents 1 or, most preferably, 0.

A particularly preferred sub-group of compounds of formula I is that in which m is 0 or 1; each of $R^1$ and $R^2$ independently represents a hydrogen atom or a methyl, ethyl, propyl, pentyl, ethoxycarbonylmethyl, benzyloxycarbonylmethyl, cyclopropyl, phenyl, fluorophenyl, trifluoromethylphenyl or naphthyl group, or $R^1$ and $R^2$ together represent a tetramethylene, pentamethylene or hexamethylene chain; $R^3$ and $R^4$, if present, both represent a hydrogen atom; X represents a cyano group; and n is 0.

It should also be noted that compounds of general formula I could be in any of the following isoelectronic forms:

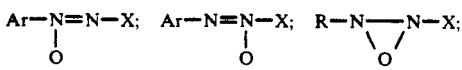

and the scope of the present invention covers such forms.

According to another aspect of the invention, there is provided a method of combating a fungus at a locus, which comprises treating the locus with a compound of general formula I as defined in any one of the preceding statements.

In the method of the invention, the locus may be an agricultural or horticultural locus, for example plants subject to or subjected to fungal attack, seeds of such plants or the medium in which such plants are growing or are to be grown. Compounds of the present invention exhibit activity against a range of important fungi, including vine downy mildew, vine grey mold and tomato early blight. A locus as described above may suitably be treated with a compound I at an application rate in the range 0.05-4 Kg/ha, preferably 0.1-1 Kg/ha.

The invention also provides the use of a compound of general formula I as defined, as a fungicide.

Further in accordance with the invention there is provided a fungicidal composition which comprises a carrier and, as active ingredient, a compound of general formula I, as defined in any of the statements above.

The invention further extends to a fungicidal composition which comprises at least two carriers and, as active ingredient, a compound of general formula I.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating biocidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5-10% w of active ingredient. Granules are usually prepared to have a size between 10 and 100 BS mesh (1.676-0.152 mm), and may be manufactured by agglomeration or impregnation techniques. Generally, granules will contain 0.5-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The composition of the invention may also contain other ingredients, for example other compounds possessing herbicidal, insecticidal or fungicidal properties.

In accordance with a further aspect of the invention, there is provided a process for the preparation of a compound of general formula I, the process comprising reacting a compound of general formula

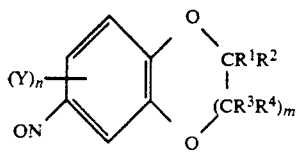

with cyanamide to form a compound of formula I wherein X represents a cyano group; and optionally derivatising that compound to produce a further novel compound of formula I.

Suitably, the reaction takes place in the presence of an organic solvent, preferably a halogenated hydrocarbon, for example, dichloromethane, and in the presence of iodobenzene diacetate or dibromoisocyanuric acid. The reaction is preferably effected at a temperature in the range $-20°$ C. to $50°$ C.

Derivatisation of the compound of formula I may, for example, be effected by standard hydrolysis, in the presence of a strong acid or strong base, to convert the cyano group to a carboxy group, or, stopping the reaction at an intermediate stage, an amido group.

Esters may be prepared by standard esterification of the resultant carboxylic acid or by acid alcoholysis of the cyano compound to form the acid salt of the imidate ester, which is reacted with water, suitably at ambient temperature, to yield the ester. Alternatively, esters may be prepared by the following route, described in greater detail in U.S. Pat. Nos. 4,558,040 and 4,550,121, (Ar representing the aryl group):

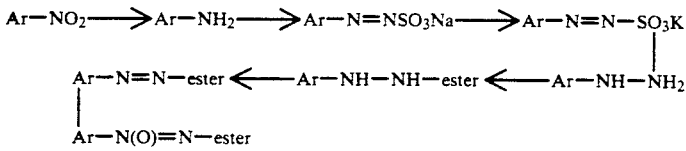

The latter two compounds may be converted to other compounds of formula I, for example, amides, acids and nitriles, by standard methods.

A compound of formula II may be prepared as follows, where Ar represents the aryl group:

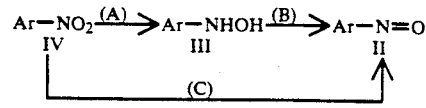

Reaction A may, for example, be effected by reaction of the nitro compound with hydrazine hydrate, in the presence of a hydrogen transfer catalyst, for example rhodium on carbon, suitably in the presence of an inert polar organic solvent, for example, tetrahydrofuran, preferably with cooling; or be effected using water, stannous chloride as reducing agent, an inert, polar organic solvent, for example tetrahydrofuran, under an inert atmosphere, for example nitrogen, in the presence of sodium acetate, suitably at ambient temperature.

Reaction B may suitably be effected by treatment of the hydroxylamine derivative with an oxidising agent, for example an $Fe^{3+}$ compound, suitably ferric chloride. The reaction may be effected in a mixed water/polar organic solvent, preferably with cooling.

Reaction C may be effected by irradiating the nitro compound, which is preferably dissolved in an inert organic solvent, for example benzene. The irradiation may be effected using a medium pressure mercury lamp.

Compounds of general formula II, III and IV, with the exception of the compound of formula IV wherein m is 0, $R^1$ and $R^2$ represent a hydrogen atom and $n=0$, are believed to be novel and they, and their preparation, constitute further aspects of the invention.

Novel compounds of formula IV may be prepared according to the processes described in JP 51086497.

Other methods suitable for preparing compounds of formula I, and further descriptions of the methods described herein, may be found in The Journal of Antibiotics, Jan. 1975, P.87–90 and June 1986, P.864–868; in Eur. J. Med. Chem.-Chim. Ther., 1982, 17, No. 5, p.482–484, and 1980, 15, No.5, p.475–478, and 1977, 12, No.1, p.59–62; in J. Chem. Soc., Chem. Commun., 1984, p.323–324; in Chem. Ind. (Milan), 1977, 59(5), p.385; in Gazetta Chimica Italians, 106, 1976, p.1107–1110; in Tetrahedron Letters, No. 38, 1974, p. 3431–3432; and in U.S. Pat. Nos. 4,558,040 and 4,550,121.

The invention will now be illustrated by the following examples.

EXAMPLE 1A

Preparation of
1,2-methylenedioxy-4-azoxycyanobenzene [m=0; $R^1=R^2=H$; n=0; X=—CN]

(i) Preparation of 1,2-methylenedioxy-4-nitrosobenzene 1,2-Methylenedioxy-4-nitrobenzene (8.3 g, 0.05 mol) was dissolved in tetrahydrofuran (150 ml) with rhodium on carbon catalyst (0.2 g) at $0°$ C. and was treated dropwise with hydrazine hydrate (2.8 g, 0.055 mol). On completion of the addition, the mixture was stirred for 1 hour and then filtered through a HYFLO (Trade Mark) filter. The resulting solution was added dropwise to a chilled, stirred solution of iron (III) chloride hexahydrate (27.5 g, 0.1 mol) in water (150 ml). On completion of the addition, water (220 ml) was added and the green precipitate was filtered off, washed with water and dried overnight under high vacuum. 1,2-Methylenedioxy-4-nitrosobenzene was obtained as a green solid (3.7 g, 50% yield) by column chromatography eluting on silica with dichloromethane. M.p. 90°–92° C. M+ (CI):152 (M+ +H)

| | | C | H | N |
|---|---|---|---|---|
| Analysis | Calc: | 55.6 | 3.3 | 9.3% |
| | Found: | 55.0 | 3.9 | 10.5% |

(ii) Preparation of
1,2-methylenedioxy-4-azoxycyanobenzene 1,2-Methylenedioxy-4-nitrosobenzene (1.5 g, 0.01 mol) obtained in (i) in dichloromethane (50 ml) and cyanamide (0.65 g) were treated dropwise at 0° C. under nitrogen with iodobenzenediacetate (3.6 g) in dichloromethane (100 ml). After stirring for 1 hour at 0° C., the solution was evaporated to dryness and 1,2-methylenedioxy-4-azoxycyanobenzene (1.7 g, 80% yield) was obtained as a yellow solid. M.p. 145°–147° C. M30 (CI) 192 (M+ +H).

| | | C | H | N |
|---|---|---|---|---|
| Analysis | Calc: | 50.3 | 2.6 | 22.0% |
| | Found: | 50.1 | 2.8 | 21.9% |

EXAMPLE 1B

Preparation of
1,2-methylenedioxy-4-azoxycyanobenzene (m=0; $R^1=R^2=H$; n=0; X=—CN)

1,2-Methylenedioxy-4-nitrosobenzene (0.6 g, 0.004 mol) obtained in Example 1A (i) was dissolved in dichloromethane (20 ml) and cyanamide (0.17 g) was added. At 0° C., dibromoisocyanuric acid was added under nitrogen in several portions. The mixture was then stirred for ½ hour at 0° C. and 1 hour at ambient temperature. The resulting yellow suspension was filtered and concentrated to dryness. Column chromatography on silica using toluene as eluant yielded 0.6 g 1,2-methylenedioxy-4-azoxycyanobenzene (79% yield) as a yellow powder.

EXAMPLES 2 to 17

By processes similar to those described in Examples 1 and 2 above, further compounds according to the invention were prepared as detailed in Table I below. In this table the compounds are identified by reference to formula I. Melting point, mass spectroscopy (m/e), C, H, N analysis data and NMR data for the compounds of Examples 2 to 17 are given in Table IA below.

TABLE I

| Example No. | m | $R^1$ | $R^2$ | $R^3$ | $R^4$ | X | n | Y |
|---|---|---|---|---|---|---|---|---|
| 2 | 0 | —CH$_2$CH$_2$CH$_2$CH$_2$CH$_2$— | | — | — | CN | 0 | — |
| 3 | 0 | —CH$_3$ | —CH$_2$COOC$_2$H$_5$ | — | — | CN | 0 | — |
| 4 | 0 | —CH$_2$CH$_2$CH$_2$CH$_2$— | | — | — | CN | 0 | — |
| 5 | 0 | —CH$_3$ | Phenyl | — | — | CN | 0 | — |
| 6 | 0 | —CH$_3$ | —CH$_3$ | — | — | CN | 0 | — |
| 7 | 0 | -$^n$C$_3$H$_7$ | -$^n$C$_3$H$_7$ | — | — | CN | 0 | — |
| 8 | 0 | —CH$_3$ | -$^n$C$_5$H$_{11}$ | — | — | CN | 0 | — |
| 9 | 0 | -$^i$C$_3$H$_7$ | -$^i$C$_3$H$_7$ | — | — | CN | 0 | — |
| 10 | 0 | —CH$_3$ | Cyclopropyl | — | — | CN | 0 | — |
| 11 | 0 | —CH$_3$ | 3-CF$_3$ Phenyl | — | — | CN | 0 | — |
| 12 | 0 | —H | 4-F Phenyl | — | — | CN | 0 | — |
| 13 | 0 | —C$_2$H$_5$ | -$^n$C$_3$H$_7$ | — | — | CN | 0 | — |
| 14 | 0 | —CH$_2$CH$_2$CH$_2$CH$_2$CH$_2$CH$_2$— | | — | — | CN | 0 | — |
| 15 | 0 | —CH$_3$ | naphth-2-yl | — | — | CN | 0 | — |
| 16 | 0 | —CH$_3$ | —CH$_2$COOC$_6$H$_5$ | — | — | CN | 0 | — |
| 17 | 1 | H | H | H | H | CN | 0 | — |

TABLE IA

| Ex. No. | M. pt. | m/e | Analysis % C Calc. Found | H Calc. Found | N Calc. Found | $^1$H-NMR (δ = ppm) Solvent = CDCl$_3$ except Ex. 17 where solvent = CD$_3$COCD$_3$ |
|---|---|---|---|---|---|---|
| 2 | 76 | 259 | 60.2 / 59.9 | 5.1 / 5.2 | 16.2 / 16.4 | 1.52, 1.75, 1.83 (10H, m, 6xCH$_2$), 6.78, 7.55 7.87(3H, Ar—H) |
| 3 | 77 | 291 | 53.6 / 53.9 | 4.5 / 4.7 | 14.4 / 14.5 | 1.20(3H, t, ester-CH$_3$), 1.82(3H, s, CH$_3$), 3.00 (2H, s, COCH$_2$), 4.12(2H, q, ester-CH$_2$), 6.80, 7.61, 7.88 (3H, Ar—H) |
| 4 | 44–48 | 245 | 58.8 / 58.8 | 4.5 / 4.7 | 17.1 / 17.0 | 1.85, 2.12(8H, m, 5xCH$_2$), 6.77, 7.58, 7.87 (3H, Ar—H) |
| 5 | 52–55 | 281 | 64.1 / 64.4 | 3.9 / 4.2 | 14.9 / 15.1 | 2.05(3H, CH$_3$), 6.87, 7.38, 7.53, 7.70, 7.92(8H, Ar—H) |
| 6 | 68 | 219 | 54.8 / 54.7 | 4.1 / 4.3 | 19.2 / 19.3 | 1.73(6H, s, 2xCH$_3$), 6.68, 7.58, 7.77(3H, Ar—H) |
| 7 | oil | 275 | 61.1 / 61.2 | 6.2 / 6.4 | 15.3 / 15.1 | 0.92, 1.45, 1.90(1H, m, 4xCH$_2$, 2xCH$_3$), 6.75, 7.53, 7.78(3H, Ar—H) |
| 8 | oil | 275 | 61.1 / 61.0 | 6.2 / 6.2 | 15.3 / 14.9 | 0.87, 1.30, 1.42, 1.67, 1.93(14H, 4xCH$_2$, 2xCH$_3$), 6.78, 7.53, 7.88(3H, Ar—H) |
| 9 | 88 | 275 | 61.1 | 6.2 | 15.2 | 0.93(12H, d, 4xCH$_3$), 2.28(m, 2xCH), 6.70, 7.50, |

TABLE IA-continued

| Ex. No. | M. pt. | m/e | C Calc. Found | H Calc. Found | N Calc. Found | ¹H-NMR (δ = ppm) Solvent = CDCl₃ except Ex. 17 where solvent = CD₃COCD₃ |
|---|---|---|---|---|---|---|
| 10 | oil | 245 | 60.3 58.8 59.1 | 6.2 4.5 4.8 | 14.4 17.1 16.1 | 7.81(3H, Ar—H) 0.58, 1.40(5H, m, cyclopropyl C₃H₅), 1.72(3H, s, CH₃), 6.77, 7.54, 7.87(3H, Ar—H) |
| 11 | oil | 349 | 55.g0 55.5 | 2.9 3.4 | 12.0 11.2 | 1.98(3H, s, CH₃), 6.82, 7.48, 7.50-7.65, 7.86(7H, Ar—H) |
| 12 | 93 | 285 | 59.0 59.0 | 2.8 2.8 | 14.7 14.3 | 6.90(1H, Ar—H), 7.21(1H, Ar—H), 7.50, 7.70, 7.98(6H, Ar—H) |
| 13 | oil | 261 | 59.8 59.9 | 5.8 5.9 | 16.1 15.3 | 0.95, 1.90(12H, m, CH₂/CH₃), 6.76, 7.53, 7.58(3H, Ar—H) |
| 14 | 57 | 273 | 61.5 61.5 | 5.5 5.7 | 15.4 15.1 | 1.65, 2.12(12H, m, 6xCH₂), 6.75, 7.54, 7.88(3H, Ar—H) |
| 15 |  | 331 | 68.9 69.3 | 4.0 4.0 | 12.7 12.0 |  |
| 16 |  | 351 |  |  |  |  |
| 17 | 134 | 205 | 52.7 52.7 | 3.4 3.4 | 20.5 20.3 | 4.32, 4.39(4H, m, 2xCH₂), 6.92, 7.23, 7.75(3H, Ar—H) |

EXAMPLE 18

The fungicidal activity of compounds of the invention was investigated by means of the following tests.

(a) Antisporulant activity against vine downy mildew (*Plasmopara viticola;* PVA)

The test is a direct antisporulant one using a foliar spray. The lower surfaces of leaves of whole vine plants (cv Cabernet Sauvignon) are inoculated by spraying with an aqueous suspension containing $2.5 \times 10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 1000 ppm, and the spray volume is 700 l/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct protectant activity against tomato late blight (*Phytophthora infestans;* PIP)

The test is a direct protectant one using a foliar spray. The upper leaf surfaces of tomato plants with two expanded leaves (cv. First in the field) are sprayed with the test compound at a dosage of 1000 ppm using a sprayer as described under (a). After a subsequent period of 24 hours under normal glasshouse conditions, the upper surfaces of the leaves are inoculated by spraying with an aqueous suspension containing $2 \times 10^5$ zoospores/ml. The inoculated plants are kept for 24 hours in a high humidity cabinet and 5 days under growth chamber conditions. The assessment is based on the percentage of diseased leaf area compared with that on control leaves.

(c) Direct protectant activity against broad bean grey mould (*Botrytis cinerea;* BCB)

The test is a direct protectant one using a foliar spray. The upper surfaces of leaves of broad bean plants (cv The Sutton) are sprayed with the test compound at a dosage of 1000 ppm using an automated sprayline as described under (a). 24 hours after spraying the leaves are inoculated with an aqueous suspension containing $10^5$ conidia/ml. For 4 days after inoculation plants are kept moist in a humidity cabinet at 21° C. Disease is assessed 4 days after inoculation, based on the percentage of leaf surface area covered by lesions.

(d) Activity against wheat leafspot (*Leptosphaeria nodorum;* LN.)

The test is a direct therapeutic one, using a foliar spray. Leaves of wheat plants (cv Norman), at the single leaf stage, are inoculated by spraying with an aqueous suspension containing $1 \times 10^6$ spores/ml. The inoculated plants are kept for 24 hours in a high humidity compartment prior to treatment. The plants are sprayed with a solution of the test compound at a dosage of 1000 ppm using an automated sprayline as described under (a). After drying, the plants are kept for 6-8 days at 22° C. and moderate humidity, followed by assessment. Assessment is based on the density of lesions per leaf compared with that on leaves of control plants.

(e) Activity against barley powdery mildew (*Erysiphe graminis* f.sp. hordei; EG)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1000 ppm using an automated sprayline as described under (a). After drying, plants are returned to a compartment at 20°-25° C. and moderate humidity for up to 7 days, followed by assessment. Assessment is based on the percentage of leaf area covered by sporulation compared with that on leaves of control plants.

(f) Activity against wheat brown rust (*Puccinia recondite;* PR)

The test is a direct protectant one using a foliar spray. Wheat seedlings (cv Avalon) are grown to the 1-1½ leaf stage. The plants are then sprayed with the test compound at a dosage of 1000 ppm using an automated sprayline as described under (a). Test compounds are applied as solutions or suspensions in a mixture of acetone and water (50:50 v/v) containing 0.04% surfactant ("TWEEN 20"-Trade Mark). 18-24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°-22° C. Thereafter, the plants are kept in ambient glasshouse conditions, that is, in moderate relative humidity and at a temperature of 20° C. The disease is assessed 10 days after inoculation on the basis of the percentage of the plant covered by sporulating pustules compared with that on the control plants.

(g) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"-Trade Mark). One day after treatment the seedlings are inoculated by spraying the leaf upper surfaces with a suspension of *A. solani* conidia containing $10^4$ spores/ml. For 4 days after inoculation plants are kept moist in a humidity compartment at 21° C. Disease is assessed 4 days after inoculation, based on the percentage of leaf surface area covered by lesions.

(h) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 50 ppm compound and 2.5% acetone. Each compartment is inoculated with a 6 mm diameter plug of agar/mycelium taken from a 14 day old culture of *P. herpotrichoides*. Plates are incubated at 20° C. for 12 days until the assessment of mycelial growth.

(k) Activity against Fusarium in-vitro (*Fusarium culmorum*; FSI)

This test measures the in vitro activity of compounds against a species of Fusarium that causes stem and root rots. The test compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp.. Plates are incubated at 20° C. for 5 days and radial growth from the plug is measured.

(j) Activity against Rhizoctonia in-vitro (*Rhizoctonia solani*: RSI)

The test measures the in-vitro activity of compounds against *Rhizoctonia solani* that causes stem and root rots. The test compound is dissolved or suspended in acetone and added into aliquots of 4 ml half strength Potato Dextrose Broth dispensed in 25-compartment petri dishes to give a final concentration of 50 ppm compound and 2.5% acetone. The fungal inoculum consists of mycelial fragments of *R. solani* grown in shaken culture flasks and added to the broth to provide $2 \times 10^3$ fragments/ml broth. Plates are incubated at 20° C. for 10 days until the assessment of mycelial growth.

The extent of disease control in all the above tests is expressed as a rating compared with either an untreated control or a diluent-sprayed-control, according to the criteria:

0 = less than 50% disease control
1 = about 50-80% disease control
2 = greater than 80% disease control The results of these tests are set out in Table II below:

TABLE II

| Compound Ex. No. | Fungicidal Activity | | | | | | | | | |
|---|---|---|---|---|---|---|---|---|---|---|
| | PVA | PIP | BCB | LN | EG | PR | AS | PHI | FSI | RSI |
| 1 | | | 2 | 2 | 1 | 2 | 2 | 2 | 2 | |
| 2 | 2 | | | 1 | | 2 | | 2 | 2 | |
| 3 | | 1 | | 2 | | 2 | | 2 | | |
| 4 | 2 | 2 | | 1 | | 2 | | 2 | 2 | |
| 5 | | | | 2 | | 2 | | 2 | 2 | |
| 6 | | 2 | | 1 | | | 1 | 2 | 2 | |
| 7 | 2 | | 1 | | | 2 | | 2 | 2 | |
| 8 | 2 | | | | | 1 | | 2 | 1 | |
| 9 | 2 | | | | | | | 1 | 2 | |
| 10 | 2 | 2 | 1 | | | | | | | 2 |
| 11 | | 2 | | | | 2 | | 1 | 1 | |
| 12 | | | | 1 | | | 2 | | | 2 |
| 13 | | | | 1 | 1 | | | 2 | | 2 |
| 14 | | | | | | | | 2 | | 2 |
| 15 | | 1 | | | | | | 1 | | |
| 16 | 1 | | | | | | | | | |
| 17 | 2 | 2 | | 2 | 2 | 2 | | 2 | 2 | |

We claim:
1. A compound of formula I:

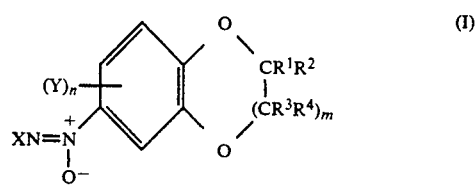

wherein m is 0 or 1;

each of $R^1$ and $R^2$, and $R^3$ and $R^4$, if present, independently represents a hydrogen or halogen atom or an optionally substituted alkyl, cycloalkyl or aryl group, or $R^1$ and $R^2$ together or $R^3$ and $R^4$ together represent an optionally substituted alkylene chain; X represents a cyano group, a group —COOH or a salt, ester or amido derivative thereof;

Y represents an alkyl group or a halogen atom; and n represents 0, 1, 2 or 3.

2. A compound as claimed in claim 1, wherein each of $R^1$ and $R^2$ independently represents a hydrogen atom or a $C_{1-6}$ alkyl, $C_{3-6}$ cycloalkyl, phenyl or naphthyl group or $R^1$ and $R^2$ together represent a $C_{4-6}$ alkylene chain, each group or chain being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl and benzyloxycarbonyl groups.

3. A compound as claimed in claim 1, wherein each of $R^3$ and $R^4$, if present, represents a hydrogen atom or a $C_{1-6}$ alkyl, $C_{3-6}$ cycloalkyl, phenyl or naphthyl group or $R^3$ and $R^4$ together represent a $C_{4-6}$ alkylene chain, each group or chain being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl and benzyloxycarbonyl groups.

4. A compound as claimed in claim 1 wherein m is 0.

5. A compound as claimed in claim 1, wherein X represents a cyano group.

6. A compound as claimed in claim 1, wherein n represents 0.

7. A compound as claimed in claim 1 wherein each of $R^1$ and $R^2$ independently represents a hydrogen atom or a methyl, ethyl, propyl, pentyl, ethoxycarbonylmethyl, benzyloxycarbonylmethyl, cyclopropyl, phenyl, fluorophenyl, trifluoromethylphenyl or naphthyl group, or $R^1$ and $R^2$ together represent a tetramethylene, pentamethylene or hexamethylene chain; $R^3$ and $R^4$, if present, both represent a hydrogen atom; X represents a cyano group; and n is 0.

8. A fungicidal composition which comprises a carrier and, as active ingredient, a compound of formula I as defined in claim 1.

9. A method of combating fungus which comprises treating plants subject to or subjected to fungal attack, seeds of such plants or the medium in which such plants are growing or are to be grown with a compound of formula I as defined in claim 1.

10. A method of combating fungus which comprises treating plants subject to or subjected to fungal attack, seeds of such plants or the medium in which such plants are growing or are to be grown with a composition as defined in claim 8.

* * * * *